United States Patent
Kauschke et al.

(10) Patent No.: US 9,050,777 B2
(45) Date of Patent: *Jun. 9, 2015

(54) CONTENDERED NONWOVEN/PULP COMPOSITE FABRIC AND METHOD FOR MAKING THE SAME

(75) Inventors: Michael Kauschke, Prien/Backham (DE); Mordechai Turi, Princeton Junction, NJ (US)

(73) Assignee: FIRST QUALITY NONWOVENS, INC., Great Neck, NY (US)

( * ) Notice: Subject to any disclaimer, the term of this patent is extended or adjusted under 35 U.S.C. 154(b) by 1650 days.

This patent is subject to a terminal disclaimer.

(21) Appl. No.: 12/226,090

(22) PCT Filed: Apr. 10, 2007

(86) PCT No.: PCT/US2007/008794
§ 371 (c)(1),
(2), (4) Date: Oct. 21, 2009

(87) PCT Pub. No.: WO2007/120629
PCT Pub. Date: Oct. 25, 2007

(65) Prior Publication Data
US 2010/0048072 A1   Feb. 25, 2010

Related U.S. Application Data

(60) Provisional application No. 60/791,010, filed on Apr. 10, 2006.

(51) Int. Cl.
*D04H 1/46* (2012.01)
*B32B 5/26* (2006.01)
(Continued)

(52) U.S. Cl.
CPC . *B32B 5/26* (2013.01); *A47L 13/16* (2013.01); *A61F 13/15203* (2013.01);
(Continued)

(58) Field of Classification Search
CPC . A47L 13/16; A47L 13/15203; A47L 13/534; A47L 13/537; A47L 13/539; B32B 2262/0253; B32B 2262/04; B32B 2262/062; B32B 2262/067; B32B 2307/726; B32B 2307/728; B32B 2432/00; B32B 2555/02; B32B 5/022; B32B 5/06; B32B 5/26; B32B 7/08; D04H 13/005; D04H 13/007; D04H 5/03
USPC .............................. 442/408, 382, 384; 28/104
See application file for complete search history.

(56) References Cited

U.S. PATENT DOCUMENTS 5,151,320 A   9/1992   Homonoff et al.
5,389,202 A * 2/1995   Everhart et al. ............... 162/103
(Continued)

FOREIGN PATENT DOCUMENTS

WO     03048440 A    6/2003
WO     2006011167 A1   2/2006

OTHER PUBLICATIONS

The International Search Report for PCT Application No. PCT/US2007/008794.
(Continued)

*Primary Examiner* — Elizabeth Cole
(74) *Attorney, Agent, or Firm* — Amster, Rothstein & Ebenstein LLP

(57) ABSTRACT

The present invention is directed to a nonwoven fabric made from a composite of nonwoven and pulp where the nonwoven has a high loft derived from a heat set three-dimensional relief structure and/or hydroengorged fiber structure. A nonwoven web is hydraulically treated to create a hydroengorged material having an increased loft. Alternatively a nonwoven web is treated to have a heat set three-dimensional relief structure. The treated web is then hydroentangled with pulp to form a cotendered nonwoven/pulp composite fabric.

38 Claims, 10 Drawing Sheets

(51) Int. Cl.

| | | |
|---|---|---|
| *A47L 13/16* | (2006.01) | |
| *A61F 13/15* | (2006.01) | |
| *A61F 13/534* | (2006.01) | |
| *A61F 13/537* | (2006.01) | |
| *A61F 13/539* | (2006.01) | |
| *D04H 5/03* | (2012.01) | |
| *D04H 13/00* | (2006.01) | |
| *B32B 5/02* | (2006.01) | |
| *B32B 5/06* | (2006.01) | |
| *B32B 7/08* | (2006.01) | |

(52) U.S. Cl.
CPC ............ *A61F 13/534* (2013.01); *A61F 13/537* (2013.01); *A61F 13/539* (2013.01); *D04H 5/03* (2013.01); *D04H 13/005* (2013.01); *D04H 13/007* (2013.01); *B32B 5/022* (2013.01); *B32B 5/06* (2013.01); *B32B 7/08* (2013.01); *B32B 2262/0253* (2013.01); *B32B 2262/04* (2013.01); *B32B 2262/062* (2013.01); *B32B 2262/067* (2013.01); *B32B 2307/726* (2013.01); *B32B 2307/728* (2013.01); *B32B 2432/00* (2013.01); *B32B 2555/02* (2013.01)

(56) References Cited

U.S. PATENT DOCUMENTS

| | | | |
|---|---|---|---|
| 6,537,644 | B1 | 3/2003 | Kauschke et al. |
| 2003/0131111 | A1 | 7/2003 | Kimura et al. |
| 2003/0211801 | A1 | 11/2003 | Putnam et al. |
| 2004/0048542 | A1* | 3/2004 | Thomaschefsky et al. ... 442/389 |
| 2005/0136778 | A1* | 6/2005 | Thomaschefsky et al. ... 442/408 |
| 2006/0057921 | A1 | 3/2006 | Turi et al. |

OTHER PUBLICATIONS

The Written Opinion for PCT Application No. PCT/US2007/008794.
Supplementary European Search Report dated Aug. 11, 2010.

\* cited by examiner

CALIPER

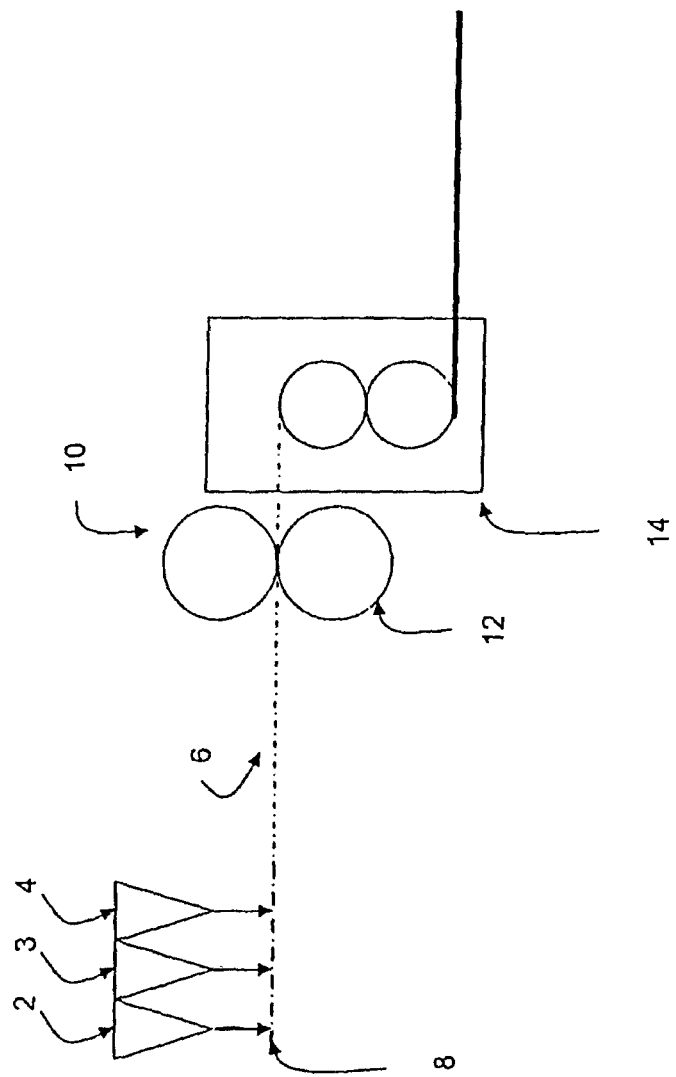

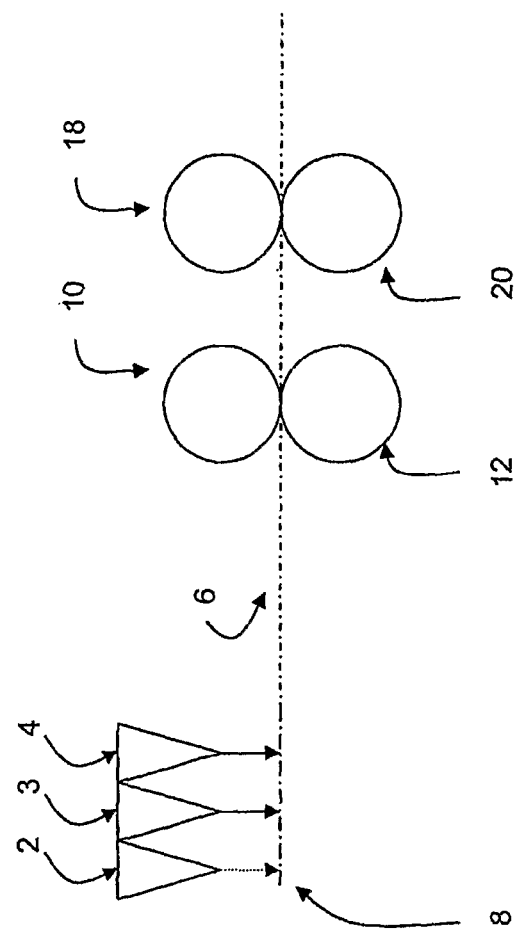

CONTENDERED NONWOVEN/PULP COMPOSITE FABRIC AND METHOD FOR MAKING THE SAME

CROSS-REFERENCE TO RELATED APPLICATION

This application claims is a U.S. national phase of PCT Application No. PCT/US2007/008794, filed Apr. 10, 2007, which claims priority to U.S. Provisional Application No. 60/791,010, filed Apr. 10, 2006.

FIELD

The present invention relates to nonwoven/pulp composites. More specifically, the present invention relates to spunbond and pulp composites having a high loft.

BACKGROUND

Composite nonwoven/pulp fabrics have been used for applications where a stable and fixed absorbent structure is required. The pulp provides absorbency and the network of fibers in the nonwoven provides a structure for retaining the pulp and significantly increasing the wet strength of the material. One use for these fabrics is as a wipe, particularly a wipe that is impregnated with a solution during manufacture and before use.

Composite nonwoven/pulp fabrics are conventionally made by depositing a pulp layer on top of a nonwoven web and subsequently hydroentangling the nonwoven and pulp together. The composite may also include a second nonwoven web that is placed on top of the pulp and is also hydroentangled.

In the past, it has not been possible to obtain a spunbond/pulp wipe having the softness and drapability of wipes made from viscose or a viscose blend. The present invention achieves a softness and drapability comparable to viscose wipes using a spunbond/pulp composite. The present invention has a further benefit in that the continuous fibers of the spunbond nonwoven provide considerably greater wet strength than wipes made with carded staple cellulosic fibers, particularly in the CD direction.

It is desirable for wipes to have a high loft, corresponding to improved softness. A recent improvement for enhancing the loft of nonwoven webs is the use of a hydroengorgement process. Hydroengorging is a process by which a nonwoven web, having been first thermally or ultrasonically bonded, is subsequently tenderized with water jets to improve the loft of the web while still retaining most of its distinct bond sites and consequently its original strength. Some fibers may be extricated from their bond sites resulting in increased thickness or caliper and in significant improvement in softness, hand and touch. During the hydroengorgement process, the fibers in the regions between bond sites are forced to move out of the flat plane of the original nonwoven and consequently the regions between bonds fluff up and gain loft and softness. The bulked structure thus produced has larger voids between bonds compared to the original nonwoven structure, as indicated by an increase in air permeability of the new structure by at least 15% compared to the original nonwovens structure. This hydroengorgement process is further detailed in U.S. Patent Application Publication No. 2006-0057921 A1, filed Sep. 10, 2004, which is hereby incorporated by reference.

An aspect of the present invention is to improve the loft and feel of spunbond/pulp composites by using hydroengorged spunbond webs. The improved loft provided by the hydroengorgement process allows for a spunbond/pulp composite that is comparable to a viscose wipe in softness and drapability and has an improved wet strength in both the machine and cross directions due to its use of spunbond fibers.

It is also desirable in particular applications to provide a nonwoven having a three-dimensional relief structure. Particular types of three-dimensional relief surfaces include regularly creped, irregularly creped, such as might be made by the MICREX process, and various regular patterns such as a waffle structure (such as might be made by a pair of heated rolls, one having male projections and the other having mating female depressions) or a bowl/cup structure (such as might be made by a pair of heated rolls, one having cup-like projections and the other having mating-bowl-like recesses). The waffle-like structure may also be referred to as "pyramids" and the bowl/cup design may be referred to as "cones."

While composites of carded nonwoven and pulp have been made using hydroentanglement and a three-dimensional forming surface to rearrange the fibers therein to produce the desired relief surface, this does not work well with composites of spunbond nonwoven and pulp. The difference is that, while the short staple fibers of the carded nonwoven are easily rearranged by hydroentanglement to assume the relief structure of a three-dimensional forming surface, the continuous fibers of a spunbond nonwoven will return substantially to their original, flattened state as soon as the composite is subjected to any tension, heat and/or pressure (for example the winding used to produce a roll of composite material). This is because the continuous fibers of a spunbond web are not free to rearrange themselves to conform to the forming surface. Further, when the composite is passed through the drying unit under tension (to dry it after hydraulic treatment), the elevated temperatures encountered therein may return the composite to its original flattened state.

Once pulp has been added to the nonwoven web or webs to form the composite fabric of spunbond and pulp, it is also generally undesirable to provide the entire composite with a three-dimensional relief structure (for example, by creping) because the additional mechanical stress may cause disintegration of the fabric structure and/or an uneconomical loss of pulp from the composite fabric.

An aspect of the present invention overcomes the aforementioned problems in forming a spunbond/pulp composite with a three-dimensional relief structure by creating a heat set three-dimensional relief structure in the spunbond nonwoven prior to formation and hydroentanglement of the composite.

The hydraulically co-entangled combination of a nonwoven having a hydroengorged or three-dimensional heat set structure with one or more other components (i.e. pulp) results in a cotendered nonwoven structure that is both bulky and soft.

SUMMARY OF THE INVENTION

An exemplary object of the present invention is a composite fabric formed from at least one nonwoven web comprising continuous fibers and pulp. The nonwoven web comprising continuous fibers is hydroengorged to improve its loft and the composite fabric including the hydroengorged web and pulp are hydraulically treated to intertwine the continuous fibers and pulp.

In a variation of the present invention at least two nonwoven webs comprising continuous fibers are hydroengorged and formed into a composite fabric.

In a variation of the present invention at least one nonwoven web is made from spunbond fibers.

In another variation of the present invention, the composite fabric includes two webs that have been hydroengorged and subsequently calendered or ultrasonically bonded with a superposing pattern prior to being hydroentangled with a pulp layer.

In an additional variation of the present invention, the nonwoven webs of the composite fabric are bonded with a bonding pattern that includes a graphic design.

In another variation of the present invention, the nonwoven webs of the composite fabric are ultrasonically embossed with a graphic design.

Another aspect of the present invention is a composite fabric formed from at least one web, comprising continuous fibers, that has been heat set so as to have a three-dimensional relief structure. The treated web and pulp are subsequently hydraulically treated to intertwine the continuous fibers and pulp.

In an additional variation of the present invention, the composite fabric including a hydroengorged web or web having a heat set three-dimensional relief structure includes a color graphic design.

In another variation of the present invention, a partially debonded nonwoven web or initially unbonded hydraulically treated web of continuous fibers is hydroentangled with pulp to form a composite fabric.

Another exemplary object of the present invention is a method for forming high loft fabric having the steps of forming a nonwoven web comprising substantially of continuous fibers and subsequently deforming the nonwoven web to create a three-dimensional relief structure at a temperature sufficiently high enough that the three-dimensional relief structure is resistant to subsequent processing steps.

An exemplary object of the present invention is a method for manufacturing a composite fabric formed from at least one hydroengorged web and a pulp layer where the hydroengorged web and pulp are hydroentangled.

Another exemplary object of the present invention is a wipe formed from a composite fabric formed from at least one nonwoven web comprising continuous fibers and pulp. The web comprising continuous fibers is treated to improve its loft and the composite fabric including the treated web and pulp are hydraulically treated to intertwine the continuous fibers and pulp.

An exemplary object of the present invention is an absorbent article containing a composite fabric formed from at least one nonwoven web comprising continuous fibers and pulp. The web comprising continuous fibers is treated to improve its loft and the composite fabric including the treated web and pulp are hydraulically treated to intertwine the continuous fibers and pulp.

BRIEF DESCRIPTION OF THE DRAWINGS

The above and related objects, features and advantages of the present invention will be more fully understood by reference to the following detailed description of the presently preferred, albeit illustrative, embodiments of the present invention when taken in conjunction with the accompanying drawing wherein:

FIG. 7 is schematic representation of a process used in hydroengorging a web of substantially continuous fibers;

FIG. 8 is schematic representation of a process used in treating a web of substantially continuous fibers to form a heat set three-dimensional relief structure;

DETAILED DESCRIPTION

Figure 1:
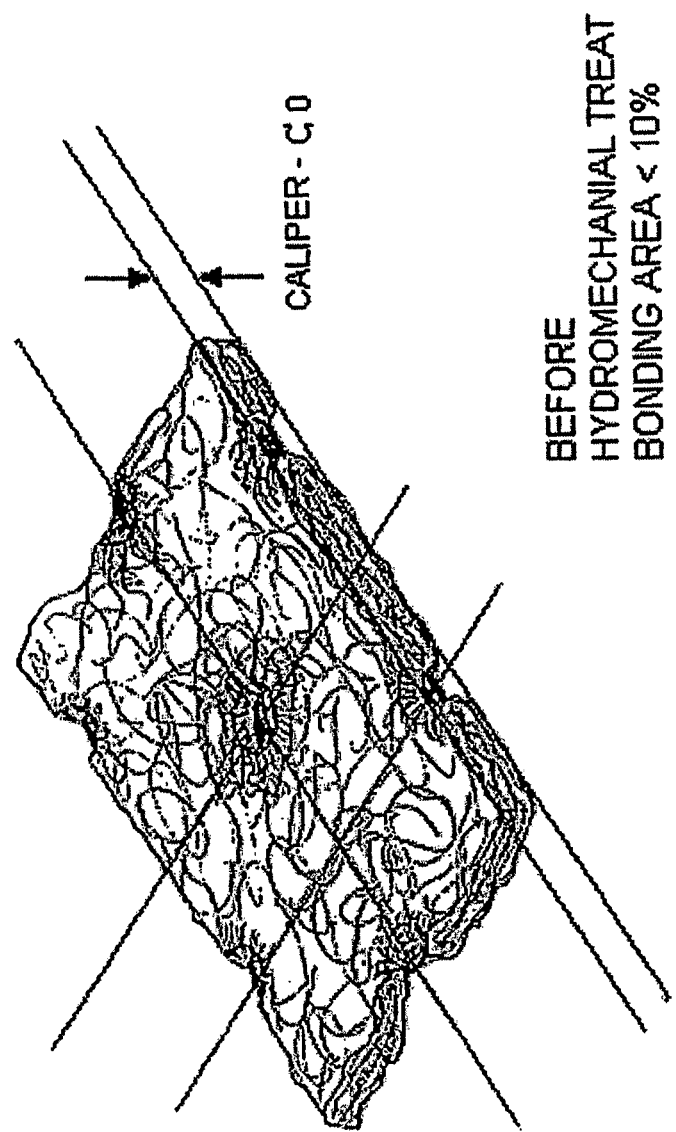
FIGS. 1 and 2 are schematic isometric views, partially in section, of a nonwoven web, before and after hydroengorgement, respectively.

The present invention is a composite fabric having one or more nonwoven webs hydroentangled with a layer of pulp, wherein the nonwoven webs have been treated to have an improved loft. Preferably the nonwoven web or webs are made from continuous fibers. More preferably, these continuous fibers are meltspun fibers which can be further characterized as spunbond or meltblown fibers based on the diameter of the fibers and the properties of the nonwovens that are formed from the fibers. For the purposes of this disclosure, "spunbond fibers" refers to continuous fibers having an average fiber diameter greater than 8 microns whereas "meltblown fibers" refers to continuous fibers having an average fiber diameter less than 8 microns, regardless of the process used to manufacture the fibers. The nonwoven webs may be formed from multiple layers of fibers, for example a spunbond-meltblown-spunbond or SMS web. The composite fabric may also have a reinforcing layer such as a scrim. Composites having one or more nonwoven webs made from carded fibers may also be used.

The fibers making up the nonwoven webs of the present invention are not limited to a particular material. For example, the fibers can be made from polyolefins such as polypropylene and polyethylene or polyester, polylactic acid (PLA), polyamide or cellulosic fibers and combinations thereof in bicomponent or multicomponent fibers. Preferably, the fibers are made from polypropylene or polyester. Bicomponent and multicomponent fibers may be used as may fibers with circular or noncircular polygonal cross sections. Splittable fibers, typically multicomponent fibers may also be used.

An advantage of using bicomponent or multicomponent fibers is that improved bonding between the fibers and improved adhesion to the pulp can be obtained. This results in increased strength in the final composite without sacrificing softness or bulk.

An advantage of using fibers with a non circular polygonal cross section is that the fiber surfaces can act as an improved filter during the hydroentanglement process and prevent pulp from washing out of the composite. Further, fiber to fiber friction is increased resulting in improved strength without sacrificing softness or bulk.

As discussed in the context of the present invention, pulp can be wood pulp fibers, but also includes other materials having similar absorbent properties. The pulp may be added in either an air-laid, wet-laid or tissue feeding process. For example, cotton linters or tissue could be used instead of or blended with wood pulp fibers. Synthetic materials such as viscose fibers may also be used alone or in a blend. The pulp may also contain polymeric or binder fibers and may contain SAP or other absorbent particulates. The use of a particular pulp material will depend on the intended use of the finished product.

Preferably, the composite fabric of the present invention includes at least one spunbond web. Composites combining only one spunbond web and a pulp layer are generally called SP fabrics whereas composites with spunbond webs on either side of a pulp layer are called SPS fabrics. The composite fabric of the present invention may also contain additional nonwoven webs or pulp layers and is not intended to be limited to the configurations described above. For example, an SMS or meltblown web may be used instead of a spunbond web. In addition, if more than one nonwoven web is used, some or all of the additional webs may not be treated to have an improved loft.

In a preferred embodiment of the invention, a hydroengorged spunbond web is used as an outer surface for a spunbond/pulp composite. In a first step, a spunbond web is hydroengorged, preferably to effect an increase of at least 50% in caliper and an increase in air permeability of at least 15%. Preferably, a layer of pulp is then air laid on top of the hydroengorged spunbond. Additional nonwoven webs, preferably one or more spunbond webs, may optionally be added to the pulp layer. If additional nonwoven webs are used, the nonwoven webs may also be hydroengorged. The composite is then hydroentangled to mix the pulp into the fiber matrix of the nonwoven webs.

Figure 2:
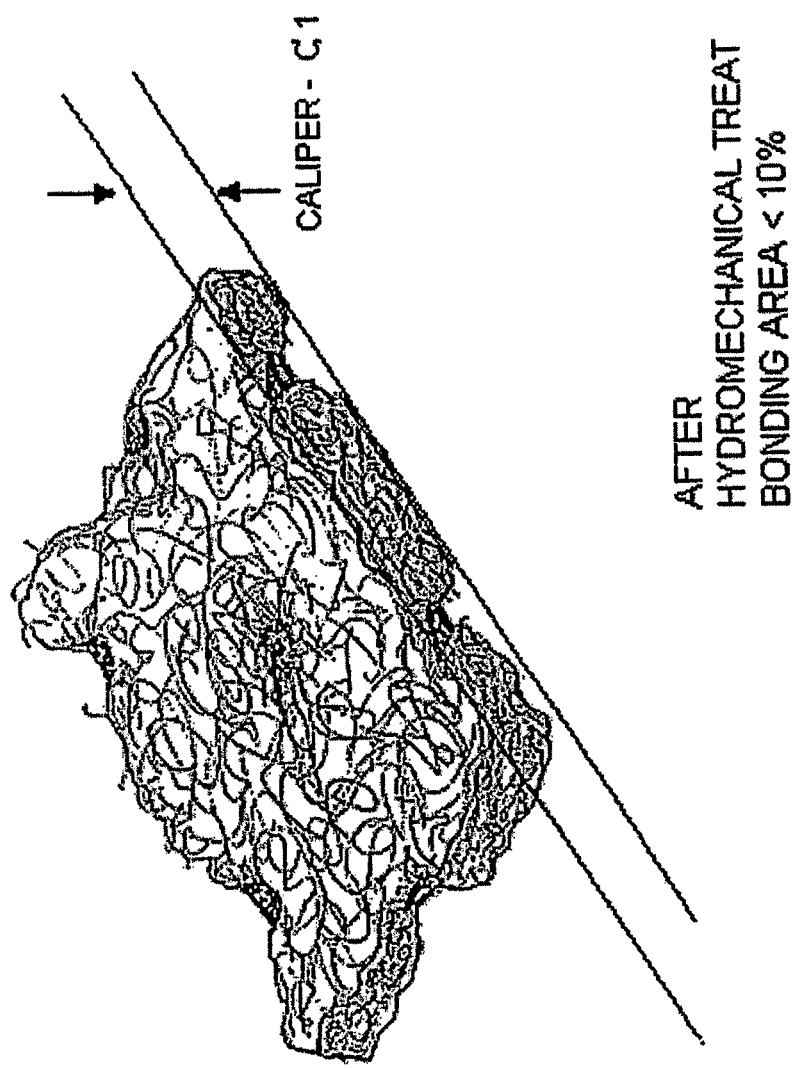

A benefit of using hydroengorged spunbond webs is that the resulting fabric has an improved softness, appearance, bulk thickness and drape, both when dry and when wet. Additionally, the improved loft of the hydroengorged spunbond aids in retaining a greater amount of pulp during the coentanglement step. FIGS. 1 and 2 show cross-sections representing a nonwoven web before and after hydroengorgement.

An alternative method for altering the surface properties of a hydroengorged web is the use of a modified screen during the hydroengorgement process. Typically, a hydroengorgement forming surface can be a drum or belt comprising a fine mesh screen for supporting a nonwoven web. This screen allows water from the water jets of the hydroengorgement machine to pass into the hydroengorgement forming surface relatively uniformly over the surface of the nonwoven web. If a thicker and more spaced apart mesh is used, water from the hydroengorgement jets will be directed into the empty areas of the mesh. As a result, the fibers of the web will be consolidated around these empty areas and the resulting web may have a variable density and the appearance of having apertures. It is also possible to add graphical elements to the hydroengorged web by adding of wire elements in the shape of the desired graphic to the screen mesh. By using a thicker wire for the graphic elements than is used in the rest of the mesh, it is believed that the fibers of the web can be distributed to create a graphic element.

Another embodiment of the present invention is nonwoven/pulp composite using a nonwoven having frangible bonds or no bonding whatsoever. Both of these types of nonwovens have an improved loft although they sacrifice strength in the process. A frangibly bonded nonwoven is a nonwoven that is bonded such that during hydraulic treatment a substantial number of bond points become completely debonded. U.S. Pat. No. 6,321,425, hereby incorporated by reference, describes such a nonwoven. U.S. Pat. No. 6,903,034 hereby incorporated by reference, describes an initially unbonded but hydraulically treated nonwoven formed from continuous fibers. In this nonwoven, the continuous fibers are entwined such that they act as bonds and provide strength to the material.

The nonwoven/pulp composite of the present invention may be embossed prior to the step of hydroentangling the pulp and nonwoven web or webs. A particular advantage of this process is that a pattern or a graphical design may be embossed or imprinted by softening or melting the fibers of the nonwoven. Exemplary graphic designs are animals or flowers. During the subsequent hydroentanglement process the bonded regions will act to reflect the water jets, thus pushing pulp away from the bonded regions. This process results in a clearly visible pattern that is enhanced by the lack of pulp and avoids the need for any subsequent embossing step.

In an embodiment of the present invention, each nonwoven web is initially thermally bonded with a pattern, preferably a cellular pattern, prior to being hydroengorged. The use of a cellular pattern has been found to be particularly beneficial because during the hydroentanglement process the pulp is pushed into the open areas of the pattern resulting in a softer, loftier fabric. Although thermal bonding is the preferred method of bonding, any commonly known bonding method, for example ultrasonic bonding, may be used.

Figure 3:
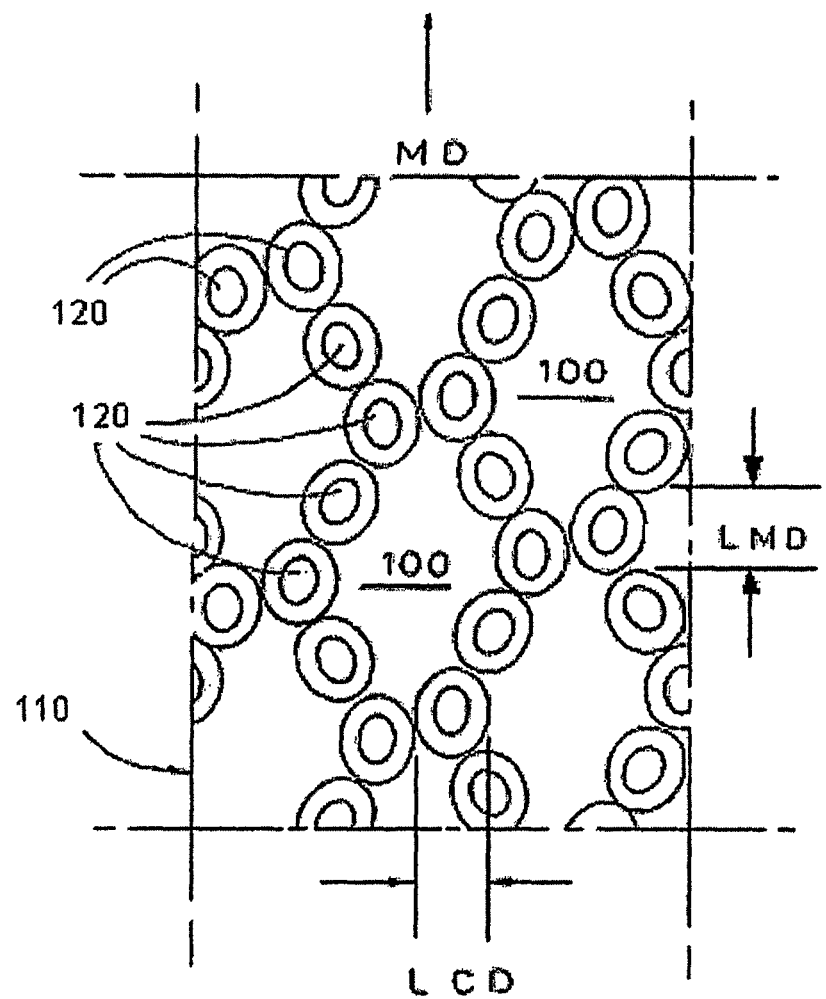
FIGS. 3 and 4 are fragmentary top plan views of an engraved bonding roll having elliptical or oval bonding points (to an enlarged scale) and the resultant fabric produced thereby (to a reduced scale), respectively.
Figure 4:
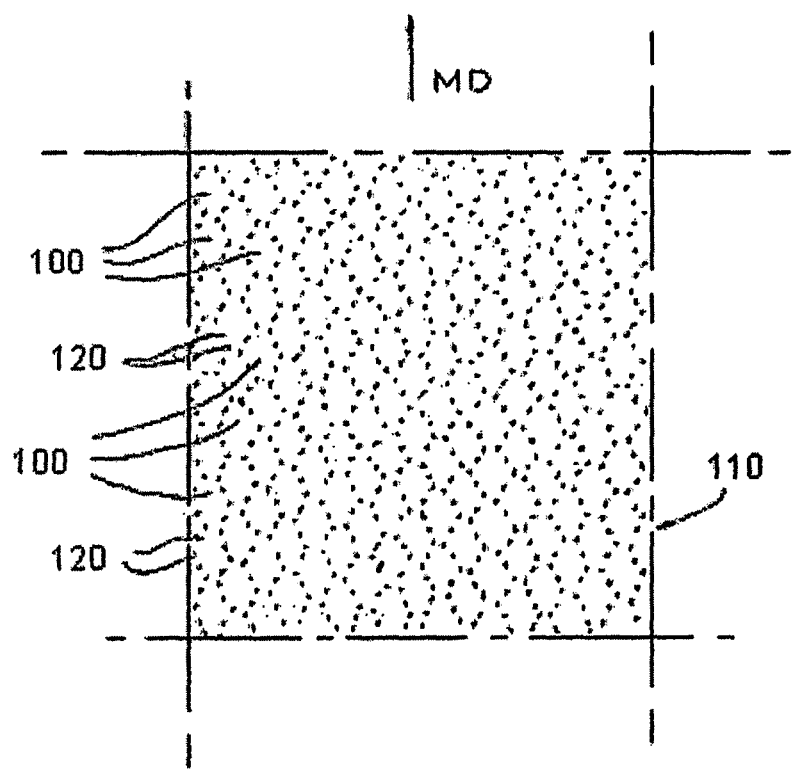

Commonly owned U.S. Pat. Nos. 6,537,644, 6,610,390, and 6,872,274, each of which is incorporated herein by reference, disclose nonwovens having a non-symmetrical pattern of fusion bonds (that is, an anisotropic or asymmetrical pattern). As disclosed in these patents, bonds in an asymmetrical pattern may have a common orientation and common dimensions, yet define a total bond area along one direction (e.g., the MD) greater than along another direction (e.g., the CD) which is oriented orthogonally to the first direction, such that the points form a uniform pattern of bond density in one direction different from the uniform pattern of bond density in the other direction. Alternatively, as also disclosed in these patents, the bonds themselves may have varying orientations or varying dimensions, thereby to form a pattern of bond density which differs along the two directions. The bonds may be simple fusion bonds or closed figures elongated in one direction. The bonds may be closed figures elongated in one direction and selected from the group consisting of closed figures (a) oriented in parallel along the one direction axis, (b) oriented transverse to adjacent closed figures along the one direction axis, and (c) oriented sets with proximate closed figures so as to form there between a closed configuration elongated along the one direction axis. A preferred pattern is the PILLOW BOND pattern shown in FIGS. 3 and 4. In FIG. 3 shows an enlarged scale view of bonding points 120 of the engraving or patterning rolls 110, whereas FIG. 4 shows a relatively reduced scale view of the patterned fabric 110 produced thereby. In both figures, the bonding points 120 form a larger closed FIG. 100.

In an embodiment of the invention, each nonwoven web is bonded with both a bonding pattern and a graphic design. This may be achieved by using an engraved bonding roll with the graphic design superimposed on the bonding pattern or through an ultrasonic process. Alternatively, two stages, for example a bonding roll and an ultrasonic process may be used. Unlike the bonding pattern, the graphic design serves a primarily ornamental function and may depict animals, plants or geometric figures and these graphic elements are greater in size than the base units of a typical bonding pattern. Generally, the graphic elements of the graphic design will extend over an area larger than 0.25 square centimeters as the greater size makes the graphic elements more discernible.

A cellular superposing pattern may also be used to post emboss the nonwoven/pulp composite. The pattern may be formed by two heated bond rolls comprising one smooth roll and one roll engraved with the pattern. Alternatively, an ultrasonic process using the same pattern anvil roll may be used. The cellular pattern may be combined with a graphic design or may stand alone. If the pattern is combined with a graphic design, the lines of the graphic design should be slightly thicker in order to improve the visibility of the graphic design. The advantage of using a closed pattern for calendering is that the superposing pattern will be in register on the nonwoven layers and thus encapsulate the pulp and bond the layers of the composite structure to prevent delamination.

In a preferred embodiment, the nonwoven/pulp composite fabric is structured so that when folded upon itself the adjacent exterior surfaces of the composite fabric do not slide on one another. This occurs because the relief patterns of the surfaces are at least partially complementary, i.e. the raised portions of one surface will fit into the depressed portions of the other surface. This configuration is sometimes described as tongue and groove. Accordingly, there is an increase in the common surface area between the two surfaces and a corresponding increase in surface friction. The benefit of this property is seen in application such as wipes where the user may fold the wipe for improved comfort. The anti-slip properties of the fabric may also be enhanced by using splittable fibers or microfibers for the anti-slip surface.

The relief pattern of the nonwoven/pulp composite fabric preferably has a average peak thickness of between 1.1 and 2 times of the average minimum thickness of the fabric. More preferably, In an alternate embodiment of the present invention, a heat set three-dimensional relief structure is applied to a nonwoven web, preferably spunbond. A layer of pulp and, optionally, another nonwoven web are then applied to the heat set three-dimensional relief nonwoven web and all of the layers are hydroentangled to form a composite fabric.

The present invention encompasses any method of creating a heat set three-dimensional relief structure on one or both of the individual webs prior to hydroentanglement or formation into a composite. A heat setting technique such as creping, microcreping (an example of which can be found in U.S. Pat. No. 4,921,643) or waffling may be used to create the three-dimensional relief pattern. Heat setting "resets" the memory of the continuous fibers of the spunbond into a desired pattern.

The temperature for heat setting is dependent on the polymer to be used. Typically, the heat setting is performed at temperatures of at least 60-120° C. More specifically, the heat set temperature should be at least 10 degrees higher than the temperature conventionally used for the drying unit, for example about 100-110° C. for polypropylene spunbond.

The three-dimensional relief structure of the present invention is preferably created after the nonwoven web is formed and bonded. If the relief structure is created during web formation or before heated calender bonding, any relief structure thus created will tend to flatten when the web is subsequently passed through a heated roll nip of a thermal bonding calender.

Once the three-dimensional relief structure is created the nonwoven web is then preferably hydroengorged to soften it and create further loft. Pulp is then deposited, for example air laid or wet laid fed, onto the web. A second nonwoven web with three-dimensional relief may be placed on top of the pulp layer. The composite is then hydroentangled. The hydroentangled composite is then de-watered and passed through an air dryer. The heat setting thus provides increased loft to the nonwoven web, and the subsequent hydroengorgement thereof provides increased softness and flexibility.

Figure 5:
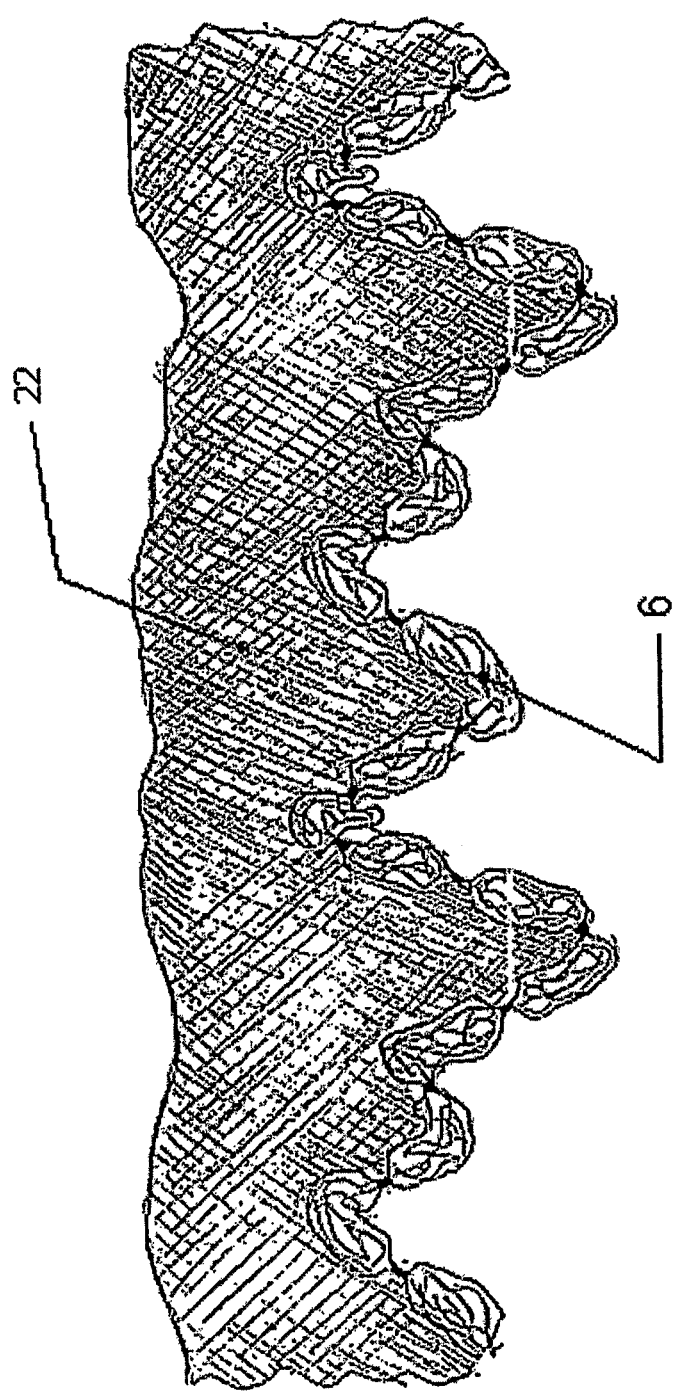
FIG. 5 is a schematic side plan view, partially in section, of a nonwoven web, having a heat set three-dimensional relief structure, and pulp deposited thereon.

A benefit of the three-dimensional relief structure is that the pulp reinforces the relief structure. A representation of this feature is shown in FIG. 5. As shown, a pulp layer 22 fills the voids of the relief structure of a nonwoven web 6 and provides additional resiliency towards deformation or flattening of the three-dimensional relief structure.

Figure 6A:
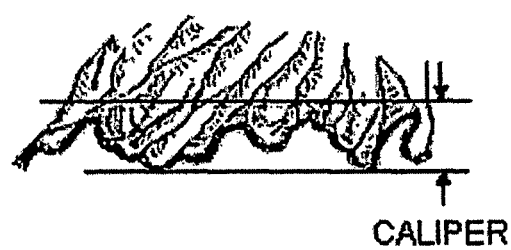
FIGS. 6A-6C are schematic isometric views, partially in section, of a nonwoven web, having a heat set three-dimensional relief structure.
Figure 6B:
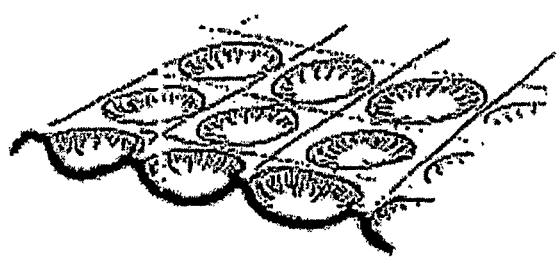
Figure 6C:
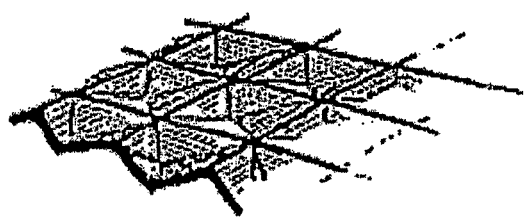

The three-dimensional relief structure thus created is preferably at least three times greater in caliper than the caliper of the precursor web. Preferably the three-dimensional relief structure consists of grooves, valleys, cups, bowls, etc. (with the relief structure top visible from one surface of the web and the relief structure bottom visible from the other side of the web) as opposed to mere surface impressions which would be visible on only one side of the web. Some examples of three-dimensional relief structures are shown in FIGS. 6A-C, namely, an irregular relief surface, a bowl relief surface and a pyramid relief surface.

The total caliper and bulk generated is a combination of (a) the three-dimensional relief structure created by the heat setting process and/or (b) any bulking created by the hydroengorging the webs prior to formation of the composite, and (c) the bulking created by hydroentanglement the composite fabric.

Note that, while a nonwoven web with a heat set three-dimensional relief structure may be hydroengorged prior to being formed into a composite, this hydroengorgement step on the individual nonwovens is not critical. The increased loft and softness of the present invention are obtained (albeit perhaps to a lesser degree) when the only hydraulic treatment is performed after formation of the composite, i.e., to integrate the composite by water needling and not on the individual pre-composite nonwoven webs.

An embodiment of the process invention is shown in FIG. 7. First, spinning beams 2 and 4 are used to form a nonwoven web 6 on conveyor belt 8. The web 6 is then bonded with calender rolls 10 and 12. The web 6 is then hydroengorged at a hydraulic treatment station 14.

In another embodiment, shown in FIG. 8, instead of undergoing hydraulic treatment, a nonwoven web 6 is passed through a pair of heated, patterned rolls 18 and 20. The rolls 18 and 20 have complementary relief patterns, i.e. a protrusion on one roll will be aligned with an indentation on the other roll. The rolls 18 and 20 are preferably heated to between about 60° C. and 120° C. In a preferred embodiment using polypropylene fibers, the rolls 18 and 20 are heated to about 100-110° C. Alternatively, the nonwoven web 6 may be creped to create an irregular relief pattern.

Figure 9:
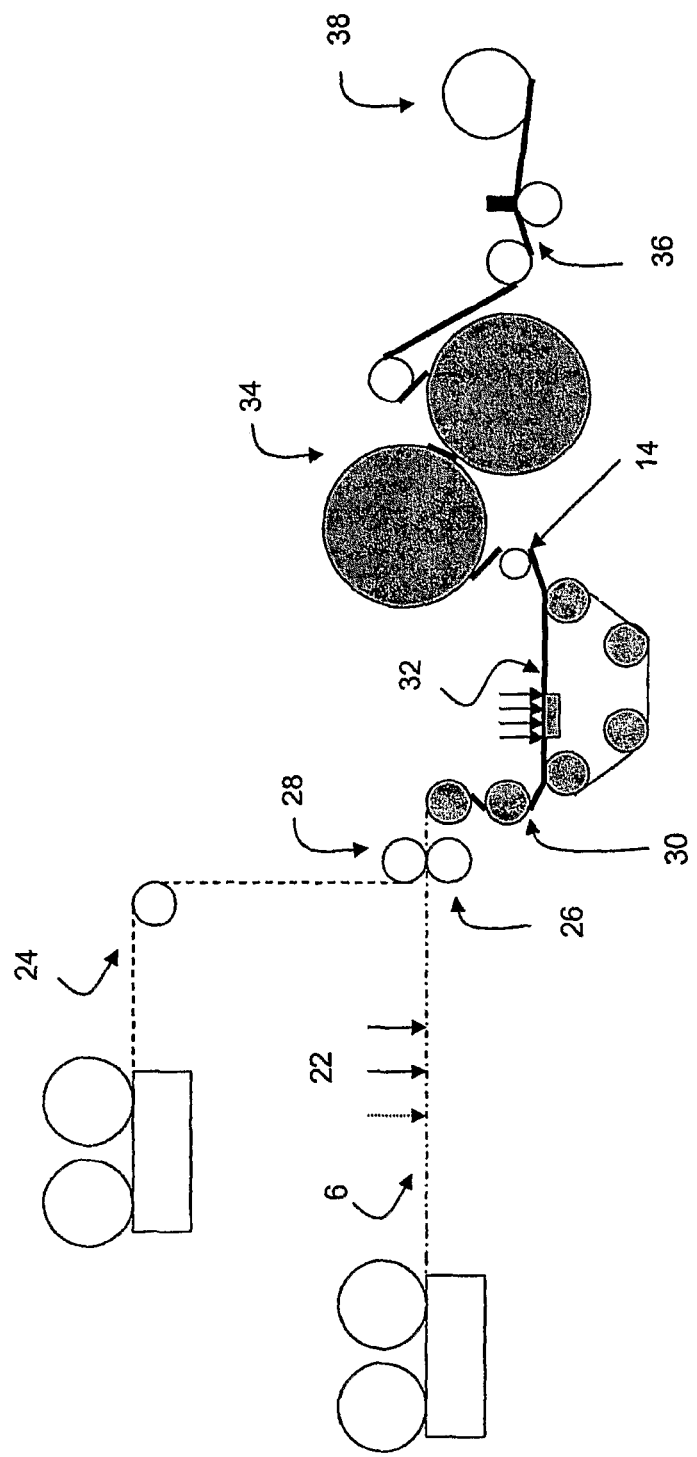
FIG. 9 is schematic representation of a process used in forming a hydroentangled composite fabric.

In an embodiment of the present invention, shown in FIG. 9, the hydroengorged or patterned web 6 may be treated with a finish at a finishing station 14 to render it softer and more condrapable, such a finish being disclosed in U.S. Pat. No. 6,632,385, which is hereby incorporated by reference, or to modify the surface energy thereof and thereby render it either hydrophobic or more hydrophobic or hydrophilic or more hydrophilic. In the case of polypropylene fibers, which are naturally hydrophobic, a hydrophilic treatment can prevent an adverse effect on the absorbency of the pulp in the finished wipe. This stage may take place prior to or after pulp deposition.

One embodiment of the present invention is an apertured cotendered nonwoven. Specifically, the cotendered nonwoven fabric of the present invention may be apertured using conventional methods to improve breathability and fluid permeability. It is not necessary for the cotendered nonwoven to be fully apertured, for example one end of the apertures may remain closed. Generally, apertures are formed through a needling process, usually with heated needles. Hot needles can melt or cause shrinkage in the fibrous material they come in contact with thus forming a clean opening in an aperture. Such openings are not always preferred, particularly as molten or conglomerated fibrous material can increase surface roughness and lead to skin irritation. By using cold needles surface roughness can be greatly reduced. Although the apertures formed through cold needling will have the general appearance of a regular aperture, the surface of the nonwoven through which the needle passes may retain some fibers.

Figure 10A:
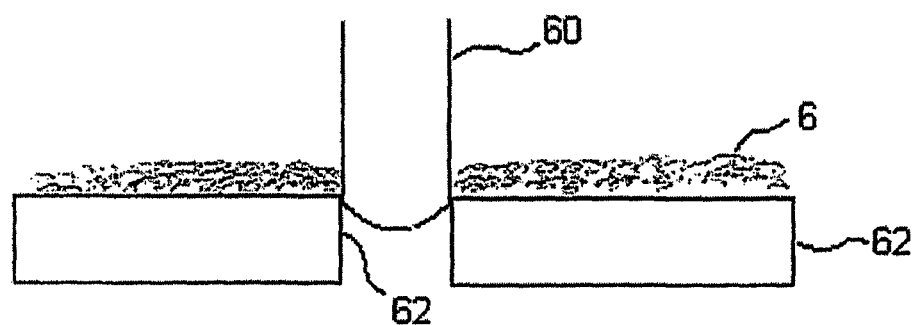
FIGS. 10A and 10B are schematic representation of cold needling processes.
Figure 10B:
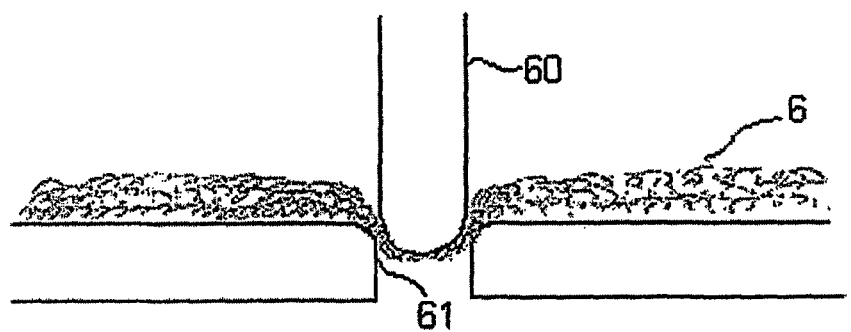

Two possible cold needling processes are shown in FIGS. 10A and 10B. In FIG. 11A the fibers of the nonwoven web 6 are pinched between a needle 60 and the edge of a receiving hole 62 thereby cutting the fibers and forming a relatively clean opening for the aperture. In FIG. 10B, the receiving hole 61 has a curved surface that prevents the fibers of the nonwoven from being cut. As a result the apertured nonwoven of FIG. 10B is has an aperture that is closed at one end.

In a pulp deposition stage, a layer of pulp 22 is deposited on the nonwoven web 6. Preferably, the pulp 22 is air-laid although a wet-laid or tissue feeding process may be used instead. A second nonwoven web 24 is deposited on top of the pulp 22. Preferably, this second nonwoven web 24 has also been treated in the same manner as the first nonwoven web 6.

Prior to being hydroentangled, the composite fabric 32 may be passed through a set of rolls 26 and 28 for forming a pattern. Preferably, this pattern is a graphic design, for example flowers. The composite fabric is then passed through a hydroentanglement station 30 which interlocks the fibers of the nonwoven webs 6 and 24 and the pulp 22 to form a cotendered composite fabric 32. The lines of the pattern formed prior to hydroentanglement can act to reflect the water jets of the hydroentanglement station 30, thus pushing pulp away from the lines and reinforcing the pattern.

After the hydroentanglement step, the cotendered composite fabric 32 is dried in a through-air dryer 34. The composite fabric may then be bonded at a bonding station 36 in order to prevent delamination. Preferably, ultrasonic bonding is used as opposed to thermal bonding as the heat of the bonding rolls can cause the composite fabric 32 to shrink. An unheated calender may be used as well. Preferably, a relatively large bond pattern is used such that the finished composite fabric 32 appears embossed. A preferable pattern is a grid pattern. In a composite fabric having only one nonwoven web, the bonding may be applied to either the pulp or nonwoven side of the composite fabric 32. Finally, the composite fabric 32 is wound into rolls on winder 38.

In a preferred embodiment, the composite fabric 32 of the present invention includes a color graphic. The color graphic may be applied directly to the composite fabric 32.

As a final processing step, the composite fabric of the present invention may be impregnated with a lotion or cleaning fluid. The improved loft of the composite fabric 32 is believed to provide improved retention capability for holding lotions and other fluids.

The cotendered composite fabric of the present invention is improved over other composite fabrics in that it has a greater loft and improved strength in both the machine and cross directions. Further, the present invention produces less lint than composite fabrics having a three-dimensional relief structure that are made using carded staple fibers instead of spunbond. Another benefit of the present invention is that the three-dimensional structure of the composite fabric reduces the surface area of the fabric that comes into contact with a user's fingers, thus providing an improved sense of dryness.

The cotendered composite fabrics of the present invention are applicable in a variety of fields. One application is to use the composite fabric as a wipe, with variations as to the construction of the wipe depending on if the desired usage is as a consumer (baby) wipe, household wipe or industrial wipe. Typically, all of these wipes would use a composite fabric having a basis weight of around 40-90 gsm. Preferably, the wipes would have an SP configuration, specifically, one spunbond web hydroentangled with pulp. Depending on the application, the wipes may be treated with cleaning solutions, fragrances, moisturizing lotions or other solutions. Household and industrial wipes may contain abrasive materials or include an external abrasive layer such as coarse meltblown fibers. Splittable fibers or microfibers may be used in the wipes to prevent the outer surfaces of the wipes from slipping when folded over onto themselves.

The cotendered composite fabrics of the present invention may also be used as a component of absorbent articles. Specifically, the composite fabrics may be used as part of the absorbent core for an absorbent article or may be used as an acquisition distribution layer or part thereof. In these application, the composite fabrics would typically have basis weight of about 20-70 gsm. Composite fabrics used in an absorbent core may include SAP. This SAP would typically be mixed with the pulp prior to formation of the composite fabric and could comprise 0-100% of the total pulp composition by weight. Preferably, an acquisition distribution layer would be made from an SP composite fabric. An SP composite fabric, preferably with a basis weight of about 20-70 gsm, could also be used for the absorbent core of a thin absorbent article such as a panty liner or sanitary napkin.

An application of the present invention is a nonwoven/pulp composite fabric for use as a printable backsheet for an absorbent article. Specifically, the pulp of the composite fabric provides a substrate which can be printed whereas the nonwoven, preferably a hydroengorged spunbond, provides a soft hand feel and strength.

Other applications of the present invention involve the use of an additive with a nonwoven/pulp composite. An oil absorbent compound can be added to improve the capacity for the composite fabric to absorb oil, for instance for use an industrial wipe. Likewise, a bleaching compound could be added for use in cleaning applications.

The cotendered composite fabrics of the present invention are also suitable for use as packaging. A sheet of composite fabric could be used as absorbent packaging for food items such as meat. A composite fabric could also be used as protective packaging as a replacement for protective packaging made from an SMS fabric. Typically, the basis weight for these applications is about 30-90 gsm. An advantage of a nonwoven/pulp composite fabric over an SMS fabric is that nonwoven/pulp composite provides more opacity. A more opaque material is more aesthetically pleasing, especially when used as packaging for meat.

An application of the present invention is a composite nonwoven/pulp composite fabric for use in electronics packaging as a replacement for silica gel. Silica gel is a desiccant used to prevent the build up of moisture. A nonwoven/pulp composite fabric could provide similar moisture absorption for a lower cost.

The teachings of the present invention may also be applied to lightweight nonwovens having a basis weight of between 5-15 gsm and more preferably about 11 gsm. At very low basis weights, structural integrity becomes an important consideration. A lightweight nonwoven/pulp composite can be made using a hydroengorged spunbond web in accordance with the present invention. Specifically, because the hydroengorged spunbond web combines both high strength and high loft, a low basis weight composite fabric will still retain its structural integrity.

Other applications which the composite fabrics of the present invention could be suitable for are filters, face masks, protective garments and medical fabrics such as fenestration drapes. Additional applications, which are not mentioned herein, may also exist and the disclosure of the aforementioned applications is not intended to be inclusive of all the potential applications.

Example 1

A layer of 15 gsm hydrophobic PP-Spunbond PB™ as supplied by First Quality Nonwovens, Hazleton, Pa., USA, was fed with a velocity of 30 m/min onto a conveyor belt and transported through an airlaid unit as offered under the tradename "Wingformer" by Celli, SA, Lucca, Italy.

With the Wingformer a layer of 30 gsm of a kraft fluff pulp that was bleached without elemental chlorine available from Weyerhaeuser, New Bern, N.C., USA under the tradename "NB416 Kraft" was evenly spread on the bottom layer spunbond.

The composite of the hydroengorged spunbond and the pulp was then exposed to an hydroentanglement unit from Rieter Perfojet, Montbonnot, France and treated on the pulp surface side with 4 injectors using pressure steps from 30 to 90 bar. During the final hydroentanglement step, the composite was treated from the spunbond side using one beam at 35 bar to push the pulp into the voids of a perforated drum sleeve having rectangular holes with a dimension of 1×1.5 mm and a hole to hole distance of 3 mm in machine direction and a hole to hole distance of 2 mm in machine cross direction to form a pulp surface with relief protrusions to increase the roughness and friction of that surface.

The wet composite was dried with an Through-Air-Dryer (from Rieter Perfojet, Montbonnot, France) in a way that the spunbond side was exposed to the surface of the drum of the dryer.

Prior to the manufacturing of the composite, the 15 gsm precursor spunbond had an caliper (INDA test method 120.1-92) average of 187 microns. The dried composite had a basis weight of 45 gsm and a caliper average of 387 microns. The composite had an average absorption capacity of 8.3 g/g. Finally, the Handle-O-Meter (Thwing-Albert) softness grade was in average of 42.3 g in the machine direction and 15.7 g in cross direction.

Example 2

A composite fabric was made according to the process used in Example 1, however the 15 gsm PP-Spunbond PB™ nonwoven layer was first hydroengorged pursuant to copending U.S. patent application Ser. No. 10/938,079.

Prior to the manufacturing of the composite, the 15 gsm precursor hydroengorged spunbond had an caliper (INDA test method 120.1-92) average of 380 microns. The dried composite had a basis weight of 45 gsm and a caliper average of 640 microns. The composite had an average absorption capacity of 9.2 g/g. Finally, the Handle-O-Meter (Thwing-Albert) softness grade was in average of 36.4 g in the machine direction and 11.9 g in the cross direction.

Example 3

A bottom layer of 11 gsm hydrophobic PP-Spunbond PB™ was fed with a velocity of 30 m/min onto a conveyor belt and transported through a Wingformer airlaid unit. With the Wingformer, a layer of 33 gsm of NB416 Kraft pulp was evenly spread on the bottom layer spunbond.

A second layer of 11 gsm hydrophobic PP-Spunbond PB™ was laid on top of the pulp layer to form a composite with a spunbond-pulp-spunbond structure.

This three-layer-composite of spunbond and pulp was then exposed to an hydroentanglement unit from RieterPerfojet, Montbonnot, France and treated on one surface side with 4 injectors using pressure steps from 35 to 50 to 90 to 90 bar.

With an additional hydroentanglement step, the composite was treated from the opposite spunbond side using one beam at 35 bar to push the pulp back into the voids of the first spunbond layer and further into the openings of the drum sleeve of Example 1 to form a pulp-like-surface with relief protrusions to increase the roughness and friction of that surface.

The wet composite was dried with an Through-Air-Dryer (from Rieter Perfojet, Montbonnot, France) in a way that the smooth spunbond surface, having substantially no pulp on the surface, was exposed to the surface of the drum of the dryer.

Prior to the manufacturing of the composite, the two 11 gsm precursor hydroengorged spunbond layers had an caliper (INDA test method 120.1-92) average of 127 and 134 microns. The dried composite had a basis weight of 55 gsm and a caliper average of 438 microns. The composite had an average absorption capacity of 6.1 g/g. Finally, the Handle-O-Meter (Thwing-Albert) softness grade was in average of 46.1 g in the machine direction and 22.4 g in the cross direction.

Example 4

A composite fabric was made according to the process used in Example 3, however the 11 gsm PP-Spunbond PB™ nonwoven layers were first hydroengorged pursuant to copending U.S. patent application Ser. No. 10/938,079.

Prior to the manufacturing of the composite, the two 11 gsm precursor hydroengorged spunbond layers had an caliper (INDA test method 120.1-92) average of 234 and 238 microns. The dried composite had a basis weight of 55 gsm and a caliper average of 560 microns. The composite had an average absorption capacity of 6.4 g/g. Finally, the Handle-O-Meter (Thwing-Albert) softness grade was in average of 32.4 g in the machine direction and 12.8 g in the cross direction.

Examples 1-4 demonstrate the advantages in terms of softness and bulk of using hydroengorged spunbond nonwovens to manufacture hydroentangled pulp composites. As hydroengorged spunbond nonwovens have an improved bulk and softness compared to standard spunbond nonwovens and further maintain these properties during conversion to hydroentangled pulp composites. As such they are advantageous for use as the base substrates for soft and bulky absorbent wipes/composites.

As the examples demonstrate, the composites structures can have a smooth surface with substantially no pulp on that surface and a second rough and high-friction surface with substantially only pulp. The high pulp surface can form a relief allowing the user to fold the wipe such that the rough surfaces of the folded wipe do not slip past each other, even when wetted with a skin care lotion. Further, the smooth surface is soft to the touch and can be used skin applications while the rough surface is used for cleaning coarse contaminated surfaces. One such dual application is a baby wipe where the smooth surface is used for the baby's skin and the rough surface is used to clean messes on the baby's clothing or surroundings.

We claim:

1. A cotendered composite fabric comprising:
   a bonded first nonwoven web comprising continuous fibers; and
   a first pulp layer substantially comprised of pulp hydroentangled with the bonded first nonwoven web;
   wherein, prior to being hydroentangled with the first pulp layer, said bonded first nonwoven web has
   a hydroengorged fiber structure.

2. The composite fabric of claim 1 wherein said first nonwoven web has a basis weight of about 11-15 gsm.

3. The composite fabric of claim 1 further comprising a reinforcing scrim.

4. The composite fabric of claim 1 wherein said composite fabric is ultrasonically embossed.

5. The composite fabric of claim 1 wherein said composite fabric is embossed by a heated calender.

6. The composite fabric of claim 1 wherein said composite fabric is embossed by an unheated calender.

7. The composite fabric of claim 1 wherein said continuous fibers comprise spunbond fibers.

8. The composite fabric of claim 1 further comprising a second nonwoven web.

9. The composite fabric of claim 8 wherein said composite fabric is ultrasonically embossed.

10. The composite fabric of claim 8 wherein said second nonwoven web comprises continuous fibers; and
    has one or more elements selected from the group consisting of (a) a heat set three-dimensional relief structure; and (b) a hydroengorged fiber structure.

11. The composite fabric of claim 10 wherein said first and second nonwoven webs have a hydroengorged fiber structure.

12. The composite fabric of claim 10 wherein said first nonwoven web has a bonding pattern comprising a graphic design.

13. The composite fabric of claim 10 wherein said first and second nonwoven webs are calendered with a superposing pattern.

14. The composite fabric of claim 13 wherein said superposing pattern comprises a graphic design.

15. The composite fabric of 14 wherein said graphic design comprises graphic elements having an average size greater than 0.25 square centimeters.

16. The composite fabric of claim 10 wherein said composite fabric comprises a color graphic design.

17. The composite fabric of 13 wherein said bonding pattern is anisotropic and biased in the machine direction.

18. A wipe comprising the composite fabric of claim 1.

19. The wipe of claim 18 wherein said wipe is a hygienic wipe.

20. The wipe of claim 18 wherein said wipe is an industrial wipe.

21. An absorbent article comprising the composite fabric of claim 1.

22. The absorbent article of claim 21 wherein said absorbent article is a sanitary napkin.

23. The absorbent article of claim 21 wherein said absorbent article is a diaper.

24. The absorbent article of claim 21 comprising an acquisition distribution layer comprising said composite fabric.

25. An absorbent sheet comprising the composite fabric of claim 1.

26. The absorbent sheet of claim 25 wherein said absorbent sheet is a laminate of said composite fabric and at least one nonwoven web.

27. A fenestration drape comprising the composite fabric of claim 1.

28. A garment comprising the composite fabric of claim 1.

29. A desiccant comprising the composite fabric of claim 1.

30. A method of manufacturing a composite fabric comprising the steps of:
    forming a first layer substantially comprised of continuous fibers;
    hydroengorging said first layer;
    depositing a second layer substantially comprised of pulp onto said first layer; and
    hydroentangling said first and second layers.

31. The method of claim 30 further comprising the steps of:
    depositing a second layer substantially comprised of pulp onto said first layer;
    forming a third layer substantially comprised of continuous fibers; and
    hydroentangling said first, second and third layers.

32. The method of 31 further comprising the step of hydroengorging said third layer.

33. The composite fabric of claim 1 wherein said fabric comprises a first surface substantially free of pulp.

34. The composite fabric of claim 8 wherein said fabric comprises a first surface substantially free of pulp.

35. The composite fabric of claim 33 wherein said fabric comprises a second surface having a rough surface profile.

36. The composite fabric of claim 34 wherein said fabric comprises a second surface having a rough surface profile.

37. The composite fabric of claim 35 wherein said second surface has features extending beyond the plane of said second surface wherein said features have a peak height of at least 20% of the caliper of said composite fabric.

38. The method of claim 30 further comprising the step of: embossing said composite fabric using a cold calender.

* * * * *

UNITED STATES PATENT AND TRADEMARK OFFICE
CERTIFICATE OF CORRECTION

| | |
|---|---|
| PATENT NO. | : 9,050,777 B2 |
| APPLICATION NO. | : 12/226090 |
| DATED | : June 9, 2015 |
| INVENTOR(S) | : Michael Kauschke and Mordechai Turi |

It is certified that error appears in the above-identified patent and that said Letters Patent is hereby corrected as shown below:

In the Title:

The title page, item (54) and in the Specification, Column 1, should read "Cotendered Nonwoven/Pulp Composite Fabric And Method For Making The Same".

Signed and Sealed this
Twenty-ninth Day of December, 2015

Michelle K. Lee
*Director of the United States Patent and Trademark Office*